United States Patent [19]
Kojima et al.

[11] Patent Number: 4,603,020
[45] Date of Patent: Jul. 29, 1986

[54] PREPARATION OF ACETYL COMPOUNDS

[75] Inventors: Hidetaka Kojima; Masahiro Kagotani, both of Himeji, Japan

[73] Assignee: Daicel Chemical Industries, Ltd., Sakai, Japan

[21] Appl. No.: 624,635

[22] Filed: Jun. 26, 1984

[30] Foreign Application Priority Data

Jul. 8, 1983 [JP] Japan ............................ 58-124342

[51] Int. Cl.$^4$ .............................................. C07C 51/54
[52] U.S. Cl. ................................... 260/549; 260/546; 502/174
[58] Field of Search ................. 260/549, 544 A, 546; 560/232; 562/519

[56] References Cited

U.S. PATENT DOCUMENTS

| | | | |
|---|---|---|---|
| 3,813,428 | 5/1974 | Paulik et al. | 562/519 |
| 3,852,346 | 12/1974 | Forster et al. | 260/408 |
| 4,252,741 | 2/1981 | Porcelli et al. | 260/549 |
| 4,374,070 | 2/1983 | Larkins et al. | 260/549 |

Primary Examiner—Natalie Trousof
Assistant Examiner—L. Hendriksen
Attorney, Agent, or Firm—Flynn, Thiel, Boutell & Tanis

[57] ABSTRACT

An O-acetyl compound, such as acetic anhydride, is prepared by carbonylating the corresponding O-methyl compound, such as methyl acetate, by heating the latter at 130° to 250° C. with carbon monoxide of a partial pressure of 1 to 100 kg/cm$^2$ G in the presence of a rhodium catalyst and a iodine compound, whereby the reaction is caused to take place in a reaction solution containing a carboxylic acid in the presence of an aluminum accelerator and a rhodium catalyst treated with hydrogen.

8 Claims, No Drawings

PREPARATION OF ACETYL COMPOUNDS

BACKGROUND OF THE INVENTION

1. Field of the Invention

This invention relates to a process for the preparation of O-acetyl compounds such as acetic anhydride by the catalytic reaction of O-methyl compounds, such as methyl acetate, as starting material, with carbon monoxide, using rhodium as a main catalyst.

Acetic anhydride is used in a large amount as a material for the production of cellulose acetate and further is useful as a material for pharmaceuticals, perfumes, dyestuffs and so on.

2. Description of Prior Art

Acetic anhydride has been conventionally produced on an industrial scale by the reaction of acetic acid with ketene obtained by thermal cracking of acetic acid.

On the other hand, in research of so-called $C_1$ chemistry, the production of acetic anhydride by the reaction of carbon monoxide with methyl acetate or dimethyl ether has been actively attempted. Particularly, in a method in which rhodium is used as a main catalyst (Japanese Patent Laid-open No. 30820/1975), the reaction proceeds under milder conditions than those in which other transition metal catalysts are used, but this method is still insufficient industrially in the reaction rate, and hence improved methods in which various reaction accelerators are added to the rhodium catalyst system have been proposed.

It is known that, in the carbonylation of methyl acetate to acetic anhydride, numerous kinds of metals act as an accelerator effective for enhancing the catalytic activity of the rhodium catalysts when added to rhodium-iodine compounds, typically, methyl iodide catalyst systems. According to Japanese Patent Laid-open No. 52017/1975 (corresponding to British Pat. No. 1468940), elements having atomic weights of at least 5 among those of Groups IA, IIA, IIIA, IVB, and VIB, non-noble metals of Group VIII, lanthanide elements, and actinide elements are considered to be effective, and particularly lithium is given as a preferred metal. Japanese Patent Laid-open No. 47922/1975 discloses a method wherein 14 kinds of metal salts such as lithium salts are used.

Non-metallic compound accelerators are also known, and organic phosphorus compounds or organic nitrogen compounds are typical. Further, combination of organic phosphorus compounds with metal compounds, such as chromium hexacarbonyl, is known (Japanese Patent Laid open No. 15403/1976).

Since, in the preparation of acetic anhydride by carbonylation, methyl acetate and acetic anhydride themselves act as a solvent, no other solvents are particularly added in most cases, as in the prior arts mentioned above. Examples wherein solvents are used, however, are also known. For example, Japanese Patent Laid open No. 47922/1975 discloses hydrocarbons, ethers, ketones, and fatty acids as inert solvents.

Aliphatic carboxylic acids sometimes serve as more than mere inert solvents. For example, Japanese Patent Laid-open No. 28980/1980 discloses cocatalysts consisting of a combination of picolinium salts with acids and, further, Japanese Patent Laid open No. 57733/1981, No. 99437/1981, and No. 99438/1981 disclose examples in which the presence of acids is essential. In all these examples, compounds containing nitrogen, phosphorus, or arsenic are essential besides the carboxylic acids.

Organic compounds such as organic phosphorus compounds or organic nitrogen compounds and metal compounds such as chromium hexacarbonyl, which are more effective among the accelerators used in the prior arts, are lacking in thermal and chemical stability as well as being expensive, and hence special devices are required in the industrial application of these accelerators to maintain the catalytic activity of them (see Japanese Patent Laid-open No. 51036/1980).

SUMMARY OF THE INVENTION

The present inventors have investigated the preparation of O-acetyl compounds from O-methyl compounds, such as methyl acetate, under mild, conditions without using organic compounds which are expensive, poor in stability and contain elements of the nitrogen group, or special compounds, such as chromium hexacarbonyl.

This invention relates to a process for the preparation of O-acetyl compounds by the carbonylation of O-methyl compounds, with carbon monoxide, in which the reaction takes place in a reaction solution containing carboxylic acids, in the presence of aluminum accelerator, an iodine compound and a rhodium catalyst treated with hydrogen.

DETAILED DESCRIPTION OF THE PREFERRED EMBODIMENTS

The carbonylation of O-methyl compounds according to the method of this invention is considered to proceed through the carbonylation of methyl iodide present in the reaction system. When the method of this invention is applied to the reaction process comprising the carbonylation of methyl iodide and the conversion with the resulting acetyl iodide of O-methyl compounds into the intended O-acetyl compounds under substantially water-free conditions, for example, to the preparation of acetic anhydride from methyl acetate or to the preparation of acetic anhydride and acetic acid from a mixture of methyl acetate and methanol, one can obtain a greatly improved reaction rate and conversion of methyl acetate and, further, the selectivity of acetic anhydride is of course good.

The method of this invention differs from that in which conventional rhodium catalysis is employed in by virtue of the use of aluminum accelerators and rhodium catalysts treated with hydrogen in the reaction liquid containing carboxylic acids, such as acetic acid. These accelerator-catalyst systems are outstandingly special in that organic nitrogen group compounds, which have conventionally been considered to be substantially indispensable for achieving an improvement of this kind of a reaction, are not required at all, and that rather better yields are obtained in the absence of organic phosphorus compounds.

As mentioned above, numerous kinds of metals are known as accelerators, including aluminum compounds such as aluminum iodide and aluminum oxide (Japanese Patent Laid-open No. 52017/1975), aluminum chloride (Japanese Patent Laid-open No. 47922/1975) and aluminum isopropoxide (Japanese Patent Laid-open No. 142234/1981). However, it has not been reported at all that these aluminum accelerators exhibit a particular effect when used in the carbonylation in combination with rhodium catalysts treated with hydrogen.

According to the method of this invention, rhodium catalysts treated with hydrogen to be combined with aluminum accelerators may be either a catalyst pretreated with hydrogen before being supplied into a carbonylation reactor, a catalyst treated with hydrogen present together with carbon monoxide in a carbonylation reactor, or a catalyst treated with nascent hydrogen generated in a catalyst solution, as in the case where the accelerator is added in the form of metallic aluminum.

Although the carbonylation of methyl acetate in the presence of hydrogen is well known (Japanese Patent Laid-open No. 65709/1976, No. 28980/1980, etc), no aluminum was used, and organic nitrogen compounds or organic phosphorus compounds were used in these patents. According to Japanese Patent Laid-open No. 52017/1975, accelerators can be used either in an elemental form such as a finely powdered or powdered metal or as a compound, and examples wherein a combination of chromium metal powder with aluminum iodide or aluminum oxide is used are disclosed.

In the preparation of a catalyst solution using metallic aluminum, the method of this invention shall be explained in comparison with this well-known art. In this prior art, no acids are added to a reaction system and therefore the chromium metal powder is considered to act as a metal itself without dissolving in the acids. The aluminum oxide is also similarly considered to act as a solid itself.

On the other hand, in the method of this invention, the catalyst liquid is prepared by using metallic aluminum in a liquid to which carboxylic acids have been added, and hence the rhodium catalyst is treated with hydrogen generated when the aluminum is dissolved.

The accelerating effect in the method of this invention is considered to be exerted on the stage of obtaining O-acetyl compounds from acetyl iodide formed by the carbonylation of methyl iodide under substantially water-free conditions rather than on the stage of carbonylation of the methyl iodide.

As described above, in the carbonylation performed using rhodium catalyst for the preparation of O-acetyl compounds from the corresponding O-methyl compounds such as methyl acetate, the employment of carboxylic acid solvent and aluminum accelerator and the reaction in the presence of hydrogen are separately known arts. The art of this invention is a novel one that exhibits superior results which have not been expected from the individual technical factors contained in these arts. An example of the effects of this invention is shown as follows. In the addition of aluminum iodide, the rhodium catalysts not treated with hydrogen did not cause the reaction to proceed at all, whereas those treated with hydrogen caused the reaction to proceed with high reactivity (Example 53 vs. 52). Further, the effects of this invention are similarly shown by comparing the examples of this invention with the example lacking a carboxylic acid (Example 3 vs. 55) or an aluminum compound (Example 2 vs. 44).

Rhodium being used as a main catalyst in the method of this invention can be fed to the reaction system as the following compounds: inorganic rhodium salts such as rhodium chloride, rhodium bromide, rhodium iodide, and rhodium nitrate, carboxylates such as rhodium acetate, rhodium acetylacetonate, rhodium-amine complex salts, organo-rhodium complexes such as trichlorotrispyridinerhodium, hydridocarbonyltris(triphenylphosphine)rhodium, chlorotris(triphenylphosphine)rhodium, chlorocarbonylbis(triphenylphosphine)rhodium, and cluster complexes such as tetrarhodium dodecacarbonyl. Although the amount of rhodium is not rigidly restricted, the rhodium is used in a concentration range from 0.1 to 50 mmol/l, preferably from 10 to 30 mmol/l, in the reaction solution.

Halogen compounds commonly used in this field, particularly iodine compounds, are used in the method of this invention. Typically methyl iodide is the most commonly used. Although the amount of methyl iodide is not rigidly restricted, methyl iodide is used in a concentration range from 0.5 to 10 mol/l, preferably from 1 to 5 mol/l, in the reaction liquid.

Aluminum accelerators may be added either as a metallic aluminum or in the form of aluminum compounds. The following aluminum compounds, for example, are used: aluminum salts of carboxylic acids such as formic acid, acetic acid, propionic acid, lauric acid, and stearic acid, aluminum alcoholates having alkoxy groups such as methoxy, ethoxy, and isopropoxy, aluminum halides having halogen atoms such as chlorine, bromine, and iodine, aluminum acetylacetonate, and aluminum nitrate. Although metallic aluminum may be used in any form of solid, leaf, finely powdered or powdered form, the powdered form is particularly preferable for handling. Further, alloys containing aluminum such as those of aluminum with nickel, cobalt, copper, and iron also may be used. The amount of aluminum is in a range from 1 to 1000 times, preferably from 1 to 100 times, particularly preferably from 5 to 50 times, that of the rhodium used, in an atomic ratio. In order to obtain a sufficient effect, aluminum is used usually above 0.1 mol/l, particularly in a range from 0.2 to 0.5 mol/l, in the reaction liquid.

In the method of this invention, the catalyst and accelerator may be recycled for use, since the rhodium catalyst is treated with hydrogen. The hydrogen treatment of rhodium catalyst, as described above, may be conducted by nascent hydrogen generated when metallic aluminum is added and dissolved, or otherwise it may be conducted by bringing the solution containing the catalyst into contact with molecular hydrogen.

The amount of hydrogen being used in the simultaneous carbonylation and hydrogen treatment is preferably in a concentration range from 1 to 30% in admixture with carbon monoxide. Although it may also be above 30%, this is not preferable because of the remarkable increase in the amounts of byproducts such as ethylidene diacetate and methane. From the standpoint of the rate of carbonylation and the amounts of the byproducts, it is particularly preferable to add hydrogen in a concentration range from 5 to 20%. The hydrogen treatment may be conducted indepently prior to the carbonylation, in which case there is little restriction to the selection of conditions.

Other components of the reaction accelerating system in the method of this invention are carboxylic acids. Acetic acid is the most common, but aliphatic carboxylic acids having 1 to 10 carbon atoms, such as propionic acid or butyric acid, alicyclic carboxylic acids, or aromatic carboxylic acids may also be used.

Carboxylic acids such as acetic acid are usually added as such to the reaction solution, but any material convertible into carboxylic acids in the reaction system may also be used. As a typical example, in the simultaneous preparation of acetic anhydride and acetic acid by carbonylation of a mixture of methyl acetate and methanol as starting materials, no acids need to be added particularly. The amount of carboxylic acids to be present in the reaction liquid is usually above 0.2 mol/l, preferably above 1 mol/l, particularly preferably above 2 mol/l. The amount of carboxylic acids may exceed half of the reaction liquid, but must not exceed 80% of the reaction liquid because the excessively large amount leads to adverse effects such as decrease in the concentration of the reactants.

In the method of this invention, the starting materials to be carbonylated are O-methyl compounds which give methyl iodide in the above reaction system, and the products are the corresponding O-acetyl compounds. Typically, the preparation of acetic anhydride by the carbonylation of methyl acetate may be mentioned. Even dimethyl ether can be converted into acetic anhydride by carbonylation.

The method of this invention may be applied to the preparation of acetic acid by the carbonylation of methanol, but the reaction proceeds at a sufficiently large rate by adding water to the reaction system even without resort to the method of this invention, when aiming at preparing only acetic acid. However, in preparing carbonylated products under substantially water-free conditions as in a case where acetic anhydride and acetic acid are simultaneously prepared by the carbonylation of a mixture of methyl acetate and methanol as starting materials, the method of this invention is useful also for the carbonylation of methanol.

Further, the method of this invention may also be applied to the carbonylation of methyl carboxylates, such as the carbonylation of methyl propionate to prepare mixed propionic acetic anhydride (which forms propionic anhydride and acetic anhydride by disproportionation).

The reaction temperature and pressure at which the method of this invention are carried out may be defined suitably referring to the conventional arts. The reaction temperature is usually in a range from 130° to 250° C., preferably from 150° to 200° C., and the pressure of carbon monoxide during the reaction is in a range from 1 to 100 kg/cm$^2$ G, preferably from 5 to 100 kg/cm$^2$ G, particularly preferably from 20 to 80 kg/cm$^2$ G.

The following embodiments to explain the method of this invention are carried out in an autoclave and the pressure is indicated by initially charged pressure. However, it is, of course, possible to carry out the method of this invention continuously, using the well known arts in this field.

The residual amount of methyl acetate and the amount of acetic anhydride formed in the reaction liquid after the completion of the reaction are determined by gas chromatography. The conversion of methyl acetate and the yield of acetic anhydride are calculated according to the following equations.

conversion of methyl acetate (%) =

$$\frac{\text{amount of methyl acetate charged (mol)} - \text{residual amount of methyl acetate after the completion of the reaction (mol)}}{\text{amount of methyl acetate charged (mol)}} \times 100$$

yield of acetic anhydride (%) =

$$\frac{\text{yield of acetic anhydride (mol)}}{\text{amount of methyl acetate charged (mol)}} \times 100$$

The reaction rate is calculated based on the pressure drop at the beginning of the reaction.

EXAMPLE 1

RhCl$_3$.3H$_2$O (0.163 g), methyl iodide (14.2 g), Aluminum powder (0.2 g), acetic acid (10.2 g) and methyl acetate (29.1 g) were charged into a 300-ml Hastelloy autoclave. The air in the autoclave was replaced by carbon monoxide and the pressure was increased to 40 kg/cm$^2$ G with carbon monoxide. The autoclave was heated to 175° C., when the reaction was initiated and continued for 60 minutes after gas absorption was observed. After the completion of the reaction, the autoclave was cooled, the residual pressure was discharged, and the reaction liquid was take up and analyzed by gas chromatography. The results were as follows: conversion of methyl acetate, 88.7%; yield of acetic anhydride, 348.3 mmol; reaction rate, 569.1 mol/mol Rh·hr.

EXAMPLE 2

(comparative)

The reaction was carried out according to the method described in Example 1 except that no aluminum was added. No gas absorption was observed at all even after prolonged heating at 175° C. and the analysis of the liquid after the completion of the reaction also showed that no acetic anhydride was formed at all.

EXAMPLE 3

(comparative)

The reaction was carried out according to the method described in Example 1 except changing the charge of methyl acetate (38.5 g) and no addition of acetic acid. The results were as follows: conversion of methyl acetate, 51.4%; yield of acetic anhydride, 267.3 mmol; reaction rate, 431 mol/mol Rh·hr.

EXAMPLE 4

The reaction was carried out according to the method described in Example 1 except using propionic acid (10.1 g) instead of acetic acid. The results were as follows: conversion of methyl acetate, 88.6%; yield of acetic anhydride, 272.6 mmol; yield of propionic anhydride, 69.0 mmol. The reaction rate calculated based on the gas absorption was 527 mol/mol Rh·hr.

EXAMPLE 5

Aluminum powder (0.6 g) was added to a mixture of RhCl$_3$.3H$_2$O (1.29 mg atom Rh), methyl iodide (4.9 ml, about 12 g), methyl acetate (40 ml), and acetic acid (24 ml) and the mixture was allowed to react at 170° C. for 60 minutes under carbon monoxide pressure (charge pressure of 50 kg/cm$^2$ G). The analysis of the reaction solution (75 ml) showed that 410.4 mmol of acetic anhydride was formed and the amount of methyl acetate decreased from 510.5 mmol (initial charge) to 100.2 mmol. The yield of acetic anhydride based on the charged methyl acetate was 80.4% and no acetyl iodide was observed in the reaction liquid. The reaction rate calculated based on the gas absorption was 7.69 mol/l·hr.

EXAMPLES 6 to 10

The reactions were carried out according to the method described in Example 5 except varying the amounts of methyl acetate (MA) and acetic acid. The results are shown in Table 1. Example 10 was comparative, where no acetic acid was added.

TABLE 1

| Example No. | MA (ml) | Acetic Acid (ml) | Reaction rate (mol/l · hr) | Yield (%) | Selectivity (%) |
|---|---|---|---|---|---|
| 6 | 24 | 40 | 7.11 | 79.6 | 100 |
| 7 | 32 | 32 | 7.97 | 87.2 | 100 |
| 5 | 40 | 24 | 7.69 | 80.4 | 100 |
| 8 | 48 | 16 | 5.55 | 67.9 | 100 |
| 9 | 56 | 8 | 4.90 | 49.7 | 94.7 |
| 10 | 64 | 0 | 3.34 | 19.3 | 80.3 |

EXAMPLE 11

The reaction was carried out according to the method described in Example 5 except using $Rh_4(CO)_{12}$ (1.29 mg atom Rh) as a rhodium catalyst and doubling the volume of methyl iodide (9.8 ml). The yield of acetic anhydride in the reaction liquid (81 ml) was 459.4 mmol and, besides, acetyl iodide (5.5 mmol) was observed. Reaction rate, 11.52 mol/l·hr; conversion of methyl acetate, 91.3%; selectivity of methyl acetate to acetic anhydride, 97.4% (yield 88.9%).

EXAMPLES 12 to 17

The reactions were carried out according to the method described in Example 5 except doubling the amount of methyl iodide (9.8 ml) and varying the amounts of methyl acetate (MA) and acetic acid. In Example 12, $Rh_4(CO)_{12}$ (1.29 mg atom Rh) was used. Example 17 was comparative, where no acetic acid was used. The results are shown in Table 2.

TABLE 2

| Example No. | MA (ml) | Acetic Acid (ml) | Reaction rate (mol/l · hr) | Yield (%) | Selectivity (%) |
|---|---|---|---|---|---|
| 12 | 24 | 40 | 6.94 | 87.3 | 100 |
| 13 | 24 | 40 | 7.24 | 94.3 | 98.5 |
| 14 | 32 | 32 | 11.10 | 93.6 | 100 |
| 11 | 40 | 24 | 11.52 | 88.9 | 97.4 |
| 15 | 48 | 16 | 10.60 | 89.1 | 100 |
| 16 | 56 | 8 | 6.48 | 71.5 | 97.2 |
| 17 | 64 | 0 | 4.93 | 47.4 | 84.2 |

EXAMPLE 18

The reaction was carried out according to the method described in Example 12 except that the amount of $Rh_4(CO)_{12}$ catalyst were decreased (0.59 mg atom Rh). The reaction rate was 5.2 mol/l·hr. The reaction rate per unit amount of the rhodium catalyst was larger than that of Example 12. Yield of acetic anhydride, 84.0%.

EXAMPLE 19

The reaction was carried out according to the method described in Example 1 except using $Rh_4(CO)_{12}$ (0.115 g) instead of $RhCl_3.3H_2O$. The results were as follows: conversion of methyl acetate 84.4%; yield of acetic anhydride 337.22 mmol; reaction rate, 546 mol/mol Rh·hr.

EXAMPLE 20

The reaction was carried out according to the method described in Example 1 except adding Ni-Al alloy (0.4 g; Al content, 50 wt. %) instead of the aluminum powder. The results were as follows: conversion of methyl acetate, 40.2%; yield of acetic anhydride, 142.0 mmol; reaction rate 227 mol/mol Rh·hr.

EXAMPLE 21

The reaction was carried out according to the method described in Example 1 except using a mixture (37.9 g) of 78:22 (wt. %) methyl acetate-methanol as a material to be carbonylated and no addition of acetic acid, and the reaction time of 90 minutes. The results were as follows: conversion of methanol, 100%; conversion of methyl acetate, 61.1%: yield of acetic acid, 267.0 mmol; yield of acetic anhydride, 244.4 mmol.

EXAMPLES 22 to 26

Various amounts of aluminum powder were added to a mixture of $RhCl_3.3H_2O$ (1.29 mg atom Rh), methyl iodide (4.9 ml, about 12 g), methyl acetate (32 ml), and acetic acid (32 ml), and the mixture was allowed to react under carbon monoxide pressure (charge, 50 kg/cm² G) at 170° C. for 60 minutes. The results are shown in Table 3. As is evident from Table 3, the reaction rate (mol/l·hr), calculated by the gas absorption at the beginning of the reaction, increased even when 0.1 g of the aluminum powder was added, and increased more largely when 0.4 to 0.6 g (about 0.2 to 0.3 mol/l) of aluminum was added, and the yield of acetic anhydride determined by the analysis of the reaction liquid increased similarly.

TABLE 3

| Example No. | Aluminum (g) | Reaction rate (mol/l · hr) | Yield (%) | Selectivity (%) |
|---|---|---|---|---|
| 22 | 0 | 1.13 | 10.5 | 59.3 |
| 23 | 0.1 | 3.01 | 27.5 | 94.7 |
| 24 | 0.4 | 6.85 | 76.2 | 100 |
| 7 | 0.6 | 7.97 | 87.2 | 100 |
| 25 | 0.9 | 7.76 | 87.3 | 98.1 |
| 26 | 1.2 | 9.10 | 89.0 | 98.8 |

EXAMPLES 27 to 30

In the case where methyl iodide was used twofold, the influence of the addition of aluminum on the results was investigated in the same manner as in Table 3. The conditions were the same as those described in Table 3 except otherwise specified. The results are shown in Table 4. The results in Table 4 showed the same effects as those of Table 3.

TABLE 4

| Example No. | Aluminum (g) | Reaction rate (mol/l · hr) | Yield (%) | Selectivity (%) |
|---|---|---|---|---|
| 27 | 0.3 | 7.52 | 77.5 | 100 |
| 14 | 0.6 | 11.1 | 93.6 | 100 |
| 28 | 0.9 | 12.0 | 91.0 | 98.2 |
| 29 | 1.2 | 12.9 | 87.7 | 97.4 |
| 30 | 1.5 | 12.1 | 83.7 | 100 |

EXAMPLES 31 to 36

The influence of the combined use of aluminum with tributylphosphine, which accelerates the reaction in the absence of aluminum, on the reaction of this invention was determined. Tributylphosphine was added in the form of $Bu_3P^+CH_3.I$ (7.3 g) and the reactions were carried out under the same conditions as those described in Table 3 except as specified otherwise. The results are shown in Table 5. As is evident from Table 5, tributylphosphine rather reduced the accelerating effect of this invention.

TABLE 5

| Example No. | Methyl iodide (ml) | Aluminum (g) | Reaction rate (mol/l · hr) | Yield (%) | Selectivity (%) |
|---|---|---|---|---|---|
| 31 | 4.9 | 0 | 1.54 | 30.2 | 100 |
| 32 | " | 0.6 | 4.55 | 85.5 | 100 |
| 33 | " | 1.2 | 4.80 | 84.0 | 100 |
| 34 | 9.8 | 0.6 | 6.10 | 89.0 | 100 |
| 35 | " | 1.2 | 8.42 | 85.5 | 94.4 |
| 36 | " | 1.5 | 8.53 | 81.5 | 90.0 |

EXAMPLES 37 to 39

The reactions were carried out under the same conditions as those described in Example 32 except using various kinds of aluminum alloys (0.3 g) (all containing 50 wt. % of Al) instead of aluminum. The results are shown in Table 6.

TABLE 6

| Example No. | Al alloy | Reaction rate (mol/l · hr) | Yield (%) | Selectivity (%) |
|---|---|---|---|---|
| 37 | Raney nickel (Kawaken K-2) | 4.63 | 74.7 | 100 |
| 38 | Raney cobalt (Kawaken #1005) | 5.71 | 76.5 | 100 |
| 39 | Raney copper (Kawaken #100) | 4.46 | 74.7 | 100 |

EXAMPLE 40

RhCl$_3$.3H$_2$O (1.29 mmol), aluminum acetate (22 mmol), methyl iodide (4.9 ml), methyl acetate (32 ml), and acetic acid (32 ml) were charged into a 300-ml Hastelloy B autoclave. The air in the autoclave was replaced by carbon monoxide, and the pressure was increased to 40 kg/cm$^2$ G with carbon monoxide and further to 45 kg/cm$^2$ G by adding hydrogen (5 kg/cm$^2$). The autoclave was heated to 170° C., and the mixture was allowed to react for 1 hr at this temperature and cooled after the completion of the reaction. The residual pressure was released, and the reaction liquid was taken up and analyzed by gas chromatography. The results are shown in Table 7.

TABLE 7

| Example No. | CO/H$_2$ (kg/cm$^2$ G) | Reaction rate (mol/l · hr) | Conversion of methyl acetate (%) | Yield of acetic anhydride (%) |
|---|---|---|---|---|
| 40 Comparative | 40/5 | 7.3 | 80.1 | 74.6 |
| 41 | 40/0 | 2.4 | 52.0 | 47.8 |
| 42 | 40/1 | 4.0 | 75.5 | 75.1 |
| 43 Comparative | 40/10 | 5.7 | 80.5 | 74.6 |
| 44 | 40/5 | 1.54 | 17.9 | 14.7 |
| 45 | 40/6 | 7.1 | 78.4 | 76.2 |
| 46 Comparative | 40/0 | 0.26 | 4.7 | 4.5 |
| 47 | 40/1 | 4.1 | 59.0 | 58.9 |
| 48 | 40/2 | 5.6 | 76.6 | 73.8 |
| 49 | 40/3 | 5.8 | 79.8 | 77.9 |
| 50 | 50/3 | 6.0 | 82.0 | 81.3 |
| 51 | 40/4 | 6.3 | 77.3 | 76.1 |
| 52 | 35/5 | 5.37 | 81.8 | 74.7 |
| 53 Comparative | 40/0 | 0 | 0 | 0 |
| 54 | 40/5 | 5.81 | 81.4 | 81.2 |
| 55 Comparative | 40/5 | 2.7 | 36.6 | 34.6 |
| 56 | 40/0 | 7.56 | 92.7 | 87.5 |

In the following Examples, the reactions were carried out according to the method described in Example 40 except otherwise specified. The results are summarized in Table 7.

EXAMPLE 41

(comparative)

No hydrogen was added.

EXAMPLES 42 and 43

Hydrogen pressure was 1 and 10 kg/cm$^2$ G, respectively.

EXAMPLE 44

(comparative)

No aluminum acetate was added.

EXAMPLE 45

The same mol of rhodium iodide as that of RhCl$_3$.3H$_2$O was used as a rhodium compound. Hydrogen pressure was 6 kg/cm$^2$ G.

EXAMPLE 46

(comparative)

The reaction conditions were the same as those described in Example 45 except no addition of hydrogen.

EXAMPLES 47 to 51

Rhodium iodide was used and the pressure of carbon monoxide and hydrogen was varied.

EXAMPLE 52

RhCl$_3$.3H$_2$O (0.93 mmol), AlI$_3$ (22 mmol), methyl iodide (4.5 ml), methyl acetate (30 ml), and acetic acid (30 ml) were charged into a 405-ml autoclave, and the pressure was increased to 35 kg/cm$^2$ G with carbon monoxide and further to 40 kg/cm$^2$ G by adding hydrogen (5 kg/cm$^2$). The mixture was allowed to react at 175° C. for 1 hr.

EXAMPLE 53

(comparative)

The pressure was raised to 40 kg/cm$^2$ G with carbon monoxide alone without added hydrogen. The reaction was carried out according to the method described in Example 52.

EXAMPLE 54

The reaction was carried out according to the method described in Example 52 except using aluminium isopropoxide (22 mmol) instead of aluminum iodide.

EXAMPLE 55

(comparative)

The reaction was carried out according to the method described in Example 40 except using acetic anhydride (32 ml) instead of acetic acid (32 ml).

EXAMPLE 56

Rhodium iodide (1.29 mmol), aluminum acetate (22 mmol), and acetic acid (32 ml) were charged into a 300-ml Hastelloy B autoclave. The air in the autoclave was replaced by carbon monoxide and the pressure was raised to 2 kg/cm$^2$ G with carbon monoxide, and further to 10 kg/cm$^2$ G by adding hydrogen (8 kg/cm$^2$). The autoclave was heated to 130° C., and the rhodium catalyst was treated with hydrogen at this temperature for 1 hr. After the auto clave was cooled, the gas was analyzed to show no formation of methane. The catalyst liquid after the hydrogen treatment was homogeneous. The residual gas was discharged, the hydrogen was removed by replacing the gas in the autoclave with carbon monoxide, and then methyl acetate (32 ml) and methyl iodide (4.9 ml) were charged. The pressure was raised to 40 kg/cm$^2$ G with carbon monoxide and the mixture was allowed to react at 170° C. for 1 hr. The conversion of methyl acetate, the yield of acetic anhydride, and the reaction rate were all high, and no ethylidene diacetate was formed. In Example 46 (comparative), the reaction was carried out according to the method described in Example 56 except using a rhodium catalyst not treated with hydrogen.

What is claimed is:

1. A process for the preparation of an O-acetyl compound by carbonylation of an O-methyl material selected from the group consisting of methyl carboxylates, dimethyl ether and mixtures thereof with methanol, which comprises: at a temperature in the range of from 130° to 250° C., reacting
   (a) carbon monoxide gas having a partial pressure of from 1 to 100 kg/cm$^2$G, with
   (b) said O-methyl material, which material is dissolved in a reaction liquid containing a catalytically effective amount of a catalyst system consisting essentially of (i) a rhodium carbonylation catalyst which has been treated with hydrogen and (ii) an iodine material providing methyl iodine in said reaction liquid so that said O-methyl material can be transformed to an acetyl iodide compound, said reaction liquid also containing an effective amount of an aluminum material effective to accelerate the transformation of said acetyl iodide compound to said O-acetyl compound, said reaction liquid also containing above 2 moles per liter of carboxylic acid in which said aluminum material is dissolved, said reaction liquid being substantially free of water and being free of organic nitrogen compounds and organic phosphorus compounds.

2. A process as claimed in claim 1, in which said rhodium carbonylation catalyst, said iodine material, said aluminum material, said carboxylic acid and said O-methyl material are placed in an autoclave, the atmosphere in said autoclave is replaced by said carbon monoxide at said partial pressure, and then said autoclave is heated to said temperature and then is maintained at said temperature until said O-acetyl compound is formed.

3. A process as set forth in claim 1, wherein said O-methyl material is methyl acetate and said O-acetyl compound is acetic anhydride.

4. A process as set forth in claim 2 in which said aluminum material is aluminum metal which is added to said carboxylic acid containing said rhodium carbonylation catalyst so that nascent hydrogen is generated and treats said rhodium carbonylation catalyst.

5. A process as set forth in claim 1 in which said rhodium carbonylation catalyst is treated with hydrogen by mixing hydrogen gas with said carbon monoxide gas and contacting said rhodium carbonylation catalyst with the mixture of said gases.

6. A process as claimed in claim 1, in which said carboxylic acid is selected from the group consisting of aliphatic carboxylic acids having 1 to 10 carbon atoms, alicyclic carboxylic acids and aromatic carboxylic acids.

7. A process as claimed in claim 4, in which said carboxylic acid is acetic acid, propionic acid or butyric acid, and said O-methyl compound is methyl acetate.

8. A process for the preparation of acetic anhydride by carbonylation of an O-methyl compound selected from the group consisting of methyl acetate and dimethyl ether, which consists essentially of: at a temperature in the range of from 130° to 250° C., reacting
   (a) carbon monoxide gas having a partial pressure of from 1 to 100 kg/cm$^2$G, with
   (b) said O-methyl compound which is dissolved in a reaction liquid containing (i) from 0.1 to 50 mmol per liter of a rhodium carbonylation catalyst and (ii) from 0.5 to 10 mol per liter of methyl iodine, said reaction liquid also containing above 2 moles per liter of acetic acid containing aluminum metal dissolved therein, the atomic ratio of aluminum to rhodium in said reaction liquid being from 1 to 1000, said rhodium carbonylation catalyst having been treated with hydrogen by contact with the nascent hydrogen generated when said aluminum metal was dissolved in said acetic acid, said reaction liquid being substantially free of water and being free of organic nitrogen compounds and organic phosphorus compound.

* * * * *

UNITED STATES PATENT AND TRADEMARK OFFICE
CERTIFICATE OF CORRECTION

PATENT NO. : 4 603 020

DATED : July 29, 1986

INVENTOR(S) : Hidetaka KOJIMA et al

It is certified that error appears in the above-identified patent and that said Letters Patent is hereby corrected as shown below:

Column 11, line 28; change "iodine" (second occurrence) to ---iodide---.

Column 12, line 34; change "iodine" to ---iodide---.

Column 12, line 45; change "compound" to ---compounds---.

Signed and Sealed this

Tenth Day of February, 1987

*Attest:*

DONALD J. QUIGG

*Attesting Officer*   *Commissioner of Patents and Trademarks*